United States Patent [19]

Gunasingham

[11] Patent Number: 5,131,999
[45] Date of Patent: Jul. 21, 1992

[54] VOLTAMMETRIC DETECTOR FOR FLOW ANALYSIS

[75] Inventor: Hari Gunasingham, Singapore, China

[73] Assignee: The National University of Singapore, Singapore, China

[21] Appl. No.: 465,060

[22] Filed: Jan. 16, 1990

[51] Int. Cl.⁵ .................................................. G01N 27/26
[52] U.S. Cl. .................................... 204/411; 204/400; 204/402; 204/403; 204/409; 204/412; 204/413; 204/415; 204/416
[58] Field of Search ............... 204/400, 402, 403, 409, 204/411, 412, 413, 415, 416, 418, 419

[56] References Cited

U.S. PATENT DOCUMENTS

| | | | |
|---|---|---|---|
| 3,334,039 | 8/1967 | Vlasak | 204/415 |
| 3,449,232 | 6/1969 | Bailey | 204/404 |
| 3,479,256 | 11/1969 | Smith et al. | 204/404 |
| 4,059,406 | 11/1977 | Fleet | 204/412 |
| 4,066,406 | 1/1978 | Pungor et al. | 204/434 |
| 4,201,646 | 5/1980 | Matson | 204/413 |
| 4,225,410 | 9/1980 | Pace | 204/412 |
| 4,496,454 | 1/1985 | Berger | 204/402 |
| 4,566,949 | 1/1986 | Berger | 204/402 |
| 4,654,127 | 3/1987 | Baker et al. | 204/412 |

Primary Examiner—T. Tung

[57] ABSTRACT

One of the fundamental limitations of voltammetric detectors in flow analysis is the problem of passivation or contamination of the working electrode. The present invention proposes a voltammetric detector based on the wall-jet principle which incorporates the concept of a replaceable working electrode. The voltammetric detector represents a significant improvement over existing detectors which are fully enclosed or sealed devices precluding easy replacement of the working electrode.

The design of the present invention provides a detector where the top is fully open and where the solution volume is maintained by the outlet positioning. The other feature of the proposed detector is an optimised geometry that provides well defined wall-jet flow characteristics which is not provided in existing detectors.

20 Claims, 6 Drawing Sheets

VOLTAMMETRIC DETECTOR FOR FLOW ANALYSIS

BACKGROUND

The present invention relates to electrochemical detectors for detecting one or more electroactive species and in particular it relates to a voltammetric detector for flowing stream analysis that employs a disposable working electrode.

In recent years there has been increasing demand for continuous monitoring flow-through electrochemical detectors. Of particular interest are voltammetric detectors which measure the faradaic current response at given applied potential, or as the applied potential is varied. Voltammetric detectors have applications which cover many fields and include for example environmental monitoring, process control, and biomedical monitoring. In particular, voltammetric detectors have found application in heavy metal monitoring, clinical chemistry and as detectors for use in high-performance liquid chromatography HPLC).

Voltammetric detectors offer considerable advantages in terms of sensitivity and selectivity over other techniques such as spectroscopy for the analysis of a wide range of chemical species. However, such systems suffer from the fundamental limitation of passivation and/or contamination of the working electrode surface caused by film formation or electrode poisoning caused by products of the electrode reaction; by the adsorption of impurities in the sample or carrier solution; or by the electro-oxidation or electro-reduction of the working electrode surface by the solvent/electrolyte. All these factors usually result in drastic changes in the detector response. The change in response depends on how badly the working electrode is passivated or contaminated. In some cases, the electrode may be rendered totally useless after the analysis of a single sample.

A number of approaches have been taken in obviating electrode passivation and contamination. For example, mechanical scrapers have been employed. These are, however, highly ineffective and can actually damage the electrode surface. They are also noisy and difficult to implement in practical voltammetric detectors. The dropping mercury electrode has been used as a way of presenting a fresh surface for each analysis. Such electrodes are, however, difficult to miniaturise and are unstable in flow systems (resulting in low signal/noise performance). Moreover, they are limited to chemical species that undergo electro-reduction. The use of potential desorption where the working electrode is poised at a potential where the adsorbed species desorb has been described in U.S. Pat. No. 4,059,406. The problem with this approach is that very strongly adsorbed species may not desorb, or the process of desorption may be too slow. Furthermore the electrode potential for desorption must be predetermined. A modification of this method has been described in U.S. Pat. No. 4,556,949 where a continuous voltage pulse train incorporating a cleaning pulse is employed. Again, a problem arises when chemical species are strongly adsorbed or when the electrode itself is oxidised or reduced by the solvent electrolyte. Further, a pulse voltage greatly decreases the signal/noise performance of the detector because of the charging current associated with pulse techniques. Continuous calibration with a standard may be employed to a limited extent to compensate for changing electrode response. However, it is not useful when the signal/noise performance is too low. Also, in general, the analytical precision is lower.

The abovementioned techniques are therefore of limited use in practical situations. In cases of severe passivation or contamination of the working electrode the only practical approach presently is to physically polish the working electrode surface when the electrode response defined by the signal-to-noise ratio is unacceptably low. Polishing is usually done manually with a fine polishing compound such as diamond paste or slurry of alumina powder of 0.05 - 0.01 micron diameter. However, this requires considerable skill on the part of the user so that a uniform and scratch-free surface is obtained.

A solution to these problems that has not been previously realised is to use a fresh electrode every time the signal/noise ratio becomes too low. Hitherto, however, the design of voltammetric detectors for continuous-flow monitoring has been based on sealed or fully enclosed cells where frequent replacement of the working electrode is not practically feasible. By way of example previously designed wall jet detectors such as the one described in U.S. Pat. Nos. 4,059,406 (Fleet), and 4,496,454/4,556,949 (Berger) or thin-layer detectors such as the one proposed by Kissinger (P. T. Kissinger, J. Chem. Educ, 60(1980)308) have provided for a fully enclosed cell where the electrodes are not disposable. Secondly, the working electrode is often fabricated as a permanent part of the cell body as described in U.S. Pat. Nos. 4,496,454 and 4,556,949 (Berger). Thirdly, present methods of fabricating the working electrodes where a solid disk of glassy carbon, gold or platinum is used, make it too costly to use a fresh electrode for each analysis. Further, there is usually considerable variation in performance from one electrode to another.

A considerable number of designs have been proposed for continuous-monitoring voltammetric detectors and the design criteria for these detectors is usually based on the voltammetric technique, measurement mode, electrode geometry, cell geometry, sample delivery and support instrumentation. The wall-jet detector or electrode is particularly suitable as a voltammetric detector because of its high sensitivity, ease of use and hydrodynamic characteristics.

However, there are other important features that sets the wall-jet configuration apart from other detector systems: One is that, by optimising the design, it is feasible to integrate the use of disposable electrodes in a flow-through detector system while maintaining well defined wall-jet hydrodynamics. This capability has not been realised in previous designs of continuous monitoring voltammetric detectors in general and in previous designs of wall-jet detectors in particular. The other feature is that it is possible to provide a reference electrode having a flowing liquid junction in close proximity to the working electrode without disturbing the working electrode response.

According to a paper by Gunasingham and Fleet published in Analytical Chemistry in July 1983 which establishes prior art in this field, when a discrete sample is injected onto the wall-jet electrode, as occurs in HPLC or flow injection analysis (FIA), dispersion of the sample takes place in the hydrodynamic boundary layer and not in the bulk solution as is usually imagined. Attempting to improve the response of wall-jet detector by decreasing cell volume is therefore ineffective and can in some instances decrease sensitivity.

The prior art publication of Gunasingham and Fleet teaches that most previous designs have overlooked fundamental principles of hydrodynamic systems and have not resulted in a structure which satisfies the above requirements. For example, when an electrode is immersed in a flowing stream, three regions of transport activity can be defined: the diffusion layer which is a stationary film adjacent to the electrode of a few hundredths of a millimeter thickness and which is the main region of electrochemical reaction; a hydrodynamic boundary layer where the flow is well defined; and the bulk solution. Because of the unique flow properties of the wall-jet, only electrochemically active species from the jet can actually reach the electrode surface thus excluding species from the bulk solution.

In general, a wall-jet voltammetric detector should satisfy a number of basic criteria in addition to being inexpensive and easy to manufacture. For example, it should be very sensitive to the concentration of electroactive material so that trace amounts can be accurately analysed. Thus, the dimensions of the diffusion layer should be minimised. The hydrodynamic boundary layer in a wall jet should be minimised because the boundary layer is the main region where dispersion of the analyte occurs and by minimising the volume of the boundary layer, band spreading is also minimised. In addition, it is important that the structure of the detector does not interfere with the flow in the boundary layer or else the disturbance in of the boundary layer can greatly affect the detection of the electroactive species and the reliability ability of the results. A further requirement is that the sample volume required to give a steady response should be minimised to permit rapid discrete injections of small volumes without the need for intermittent flushing of the cell thereby avoiding sophisticated low tolerance cell design and permitting automation of on-line voltammetric techniques.

In addition, in a wall-jet detector the free jet made to impinge upon the detector should be obtained under well defined flow conditions and the jet should be stable as defined by the Reynold's number. Furthermore, the counter electrode and reference electrode should be located as close to the working electrode as possible but not so as to interfere with the flow of the wall jet. The electrolysis efficiency should also be optimised to maximise sensitivity in applications such as in HPLC.

There are a number of proposed and known wall-jet voltammetric detectors for use in the application areas described above. However, most efforts concerned with improving existing voltammetric detector designs have focused on cell geometry and location of working electrode and counter electrodes. The general trend has been to minimise the geometric cell volume in order to maximise the ratio of the working electrode area to sample volume. Roston et. al. Analytical Chemistry Vol. 54(1982)1471A and Lunte and Kissinger, Analytical Chemistry Vol 55(1983)1458 have described some thin-layer designs which focus on low cell volume as a criteria for detector performance. A proposed wall-jet cell disclosed in U.S. Pat. No. 4,059,406 also focused on low cell volume as a key criteria for detector performance. These small volume detectors are fully enclosed or sealed devices which preclude regular replacement of the working electrode.

The other practical problem associated with existing wall-jet detectors that are fully enclosed or sealed is that of air bubbles that can get entrapped within the cell. his can lead to increased noise and reduced sensitivity and accuracy.

Because of the unique features offered by the wall-jet configuration, any design should utilise these principles of hydrodynamic operation to the fullest extent to provide an efficient wall-jet voltammetric detector.

An object of the present invention is to provide an improved wall jet detector. The detector provides four features:

i) It provides a wall jet detector which obviates and mitigates the disadvantages associated with the above-mentioned existing wall-jet detectors.

ii) It provides a detector where the cell does not have to be sealed or fully enclosed and where the solution level in the detector is defined by the outlet positioning.

iii) it exploits the inherent features provided by (i) and (ii) to enable the use of disposable electrodes thereby obviating the problem of electrode passivation/contamination in routine use without diminishing the hydrodynamic performance of the cell and iv) through the disposable electrode concept, it is feasible to employ screen printing technology to fabricate chemically coated working electrodes where specific, single layer or multi-layer reagent or membrane coatings are applied to the electrode to make it selective to specific chemical species.

v) it provides a reference electrode which employs a flowing liquid junction thereby eliminating the need for a sealed reference system.

The above features are achieved by providing a wall-jet detector having a large effective cell volume. In addition, however, the cell chamber is not sealed but is actually a well that is opened at the top. The well is partially filled with solution and configured in a way that enables easy placement of the working electrode in the form of a disposable slide. The inlet jet diameter is optimised and the outlet positioned so as to regulate the solution level in the well. The counter and reference electrodes are located in a manner that flow disruption is minimised.

Accordingly, in one aspect of the invention there is provided a wall-jet detector for detecting electrochemical species, said wall-jet detector having a detector housing defining a well which is partially filled with solution, liquid jet producing means coupled to the housing for providing a liquid jet having a jet direction into said detector well and said liquid jet producing means defining a liquid jet inlet to said detector well; a disposable working electrode fabricated on a flat rectangular slide that fits into a slot in the well, said working electrode slide that can be easily positioned in the detector well opposite to said liquid jet inlet at a predetermined distance therefrom, a said working electrode lying in plane substantially perpendicular to the direction of said liquid jet inlet, a reference electrode being coupled to the housing ahd linked to the said well, said detector housing having liquid outlet means for permitting the outflow of solution from said well the arrangement being such that in operative condition, a jet of liquid of a predetermined cross-sectional area is forced into said chamber through said liquid jet inlet means, said working electrode having an electrode cross sectional area in a range of at least five times the cross-sectional area of the liquid jet, said working electrode and said reference electrode being energised for said working electrode to detect electrochemical species in said jet impinging on said working electrode, the detector well being proportioned so that there is no interference with the boundary layer, the stability of the jet being controlled by the linear flow velocity, the inlet jet diameter and the kinematic viscosity selected so that said liquid jet has laminar flow characteristics.

In a preferred embodiment of the invention, a counter electrode is also used. The counter electrode can be fabricated on the same slide as the working electrode or it can be symmetrically placed within the chamber as a separate electrode. The working electrode can be made of a number of materials including carbon, platinum and gold; the counter electrode is made of carbon or platinum; and the reference electrode is usually a silver-silver chloride (Ag/AgCl) electrode. The housing is made of a material depending on the application. For example, Perspex is used for aqueous work and for non aqueous work a material called Kel-F is used. The preferred inlet jet diameter range is 0.1-1.0 mm and the preferred value is 0.3 mm and the preferred distance between the jet nozzle and the working electrode is 1-4 mm and the preferred diameter of the working electrode is selected empirically to give the optimum wall jet cell response but is typically 5 to 10 times the diameter of the inlet jet.

These and other aspects of the invention will be described with reference to the accompanying drawings in which.

DETAILED DESCRIPTION OF INVENTION

Reference is first made to FIGS. 1-4 of the drawings which shows a wall jet detector comprising a cell housing 10. Portions 12, 14 and the base 16 define a internal cell chamber where the top 20 is open. The chamber is normally filled with solution up to a mark defined by the position of the outlet 22 when in an operative condition. The cell housing has a threaded aperture through which is passed a threaded Teflon nozzle structure 24. The nozzle structure engages with the threaded aperture. Each of these structures also has a knurled locking 26 for securing the nozzle relative to the housing. A reference electrode 28 is similarly mounted on a side compartment of the housing.

Figure 1:
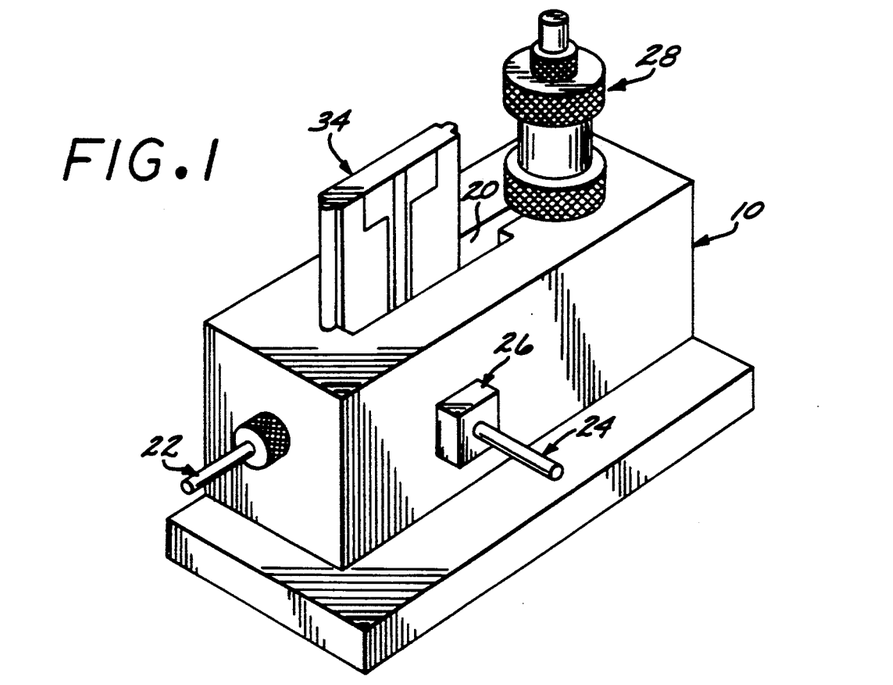
FIG. 1 is a perspective view of a wall-jet voltammetric detector in accordance with the preferred embodiment of the invention.
Figure 2:
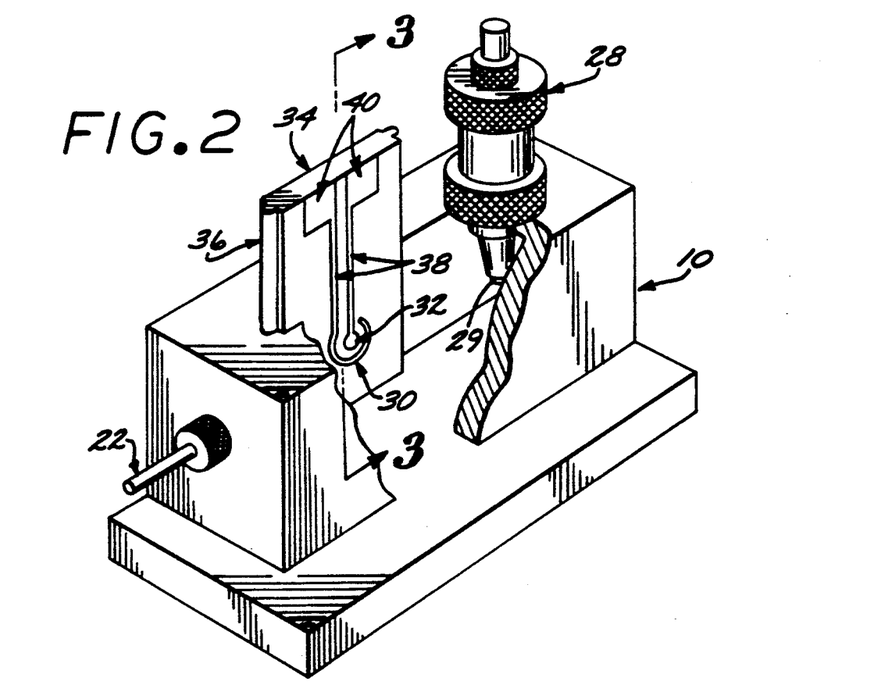
FIG. 2 is a partly broken away view of the wall-jet detector shown in FIG. 1.

The counter electrode 30 and working electrode 32 is fabricated on a rectangular slide 34 that can be slotted using the special guide 36 via the open top of the chamber. The slide 34 may be made of glass, ceramic, or plasti material. The working electrode 32 is designed to fall in place exactly opposite the nozzle outlet so that it is along the axis of the incoming jet issuing from the nozzle. The counter electrode 30 is desirably positioned symmetrically in the chamber with respect to the liquid jet inlet nozzle 24 and the working electrode 32. Each of the counter electrode 30 and reference electrode 28 is movable and each may have respective locking means associated therewith for permitting the prespective counter electrode 30 and reference electrode 28 to be moved and positioned relative to the working electrode 32. In one embodiment, two or more working electrodes 32 are provided on a single slide 34, so that each working electrode, in use, detects electroactive species at different potentials. In another embodiment, the working electrode is a micro-electrode array where the width of each electrode is between 1 and 50 micrometers. Electrical connection to the working electrode is made when the metal lead 38 meets the contact strip 40.

The inlet nozzle 24 has a nozzle bore 44 through which liquid can be passed to form a liquid jet 46 which impinges at the center of the working electrode 32. The nozzle diameter is 0.3 mm producing a liquid jet of 0.3 mm diameter. The working electrode 32 is made of conductive carbon, gold or platinum which is screen printed or mounted in some other way on the slide. The working electrode 32 may be made by screen printing organic metal ink on a glass or ceramic slide 34 and then firing the slide 34 to achieve a metal-like finish. The working electrode 32 may also be made by photolithographic and vapor deposition techniques. The working electrode 32 may be modified with various chemical coatings to make the electrode selective to specific chemical species. One example of such a coating is a mercury film, or a mercury film covered with a polymer layer. Another example of such a coating is an enzyme. The chemical coating maybe a mixture of several chemicals. The chemical coating may serve as a membrane to provide a diffusion barrier to chemical species. The electrode is connected to an amplifier for detecting electrochemical species as will be described later. The diameter of the working electrode is 3 mm and the distance between the nozzle outlet and the surface of the working electrode is 1 mm in this preferred embodiment. The reference electrode 28 is threaded and tapers to a ceramic or vycor frit 29 which provides a solid junction between the reference compartment and the bulk solution in the cell. In some applications, however, it may be preferable to do without the frit. In this case, the reference electrode internal filling solution has to be continuously fed into the reference electrode compartment. Because of the flow characteristics of the wall jet the flowing solution from the reference electrode 28 does not interfere with the working electrode reaction.

The counter electrode 30 is made of carbon or platinum and is mounted on the rectangular slide parallel to the working electrode.

Figure 3:
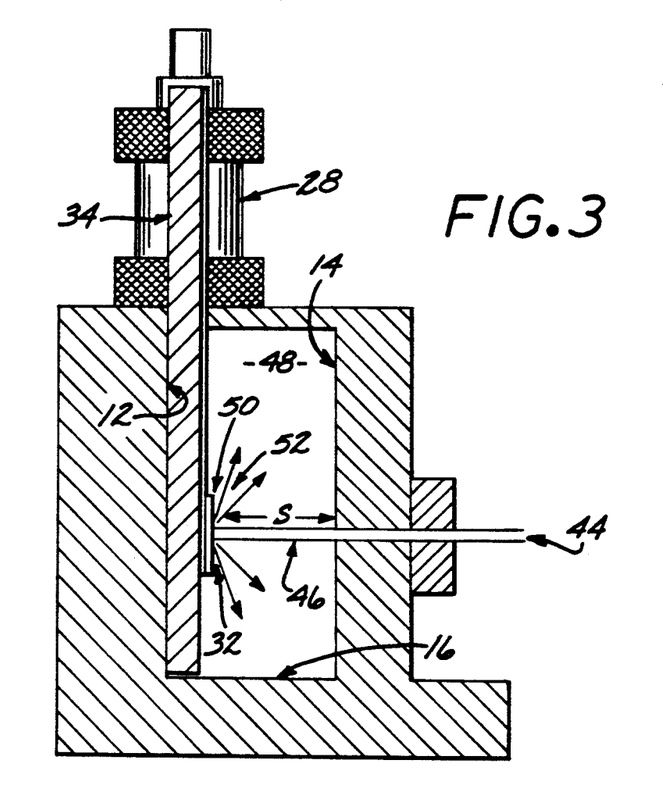
FIG. 3 is an enlarged side view of the working electrode shown diagrammatically in the in-use position with a liquid jet impinging on the working electrode.

Reference is now made to FIG. 3 of the drawings which diagramatically shows a liquid jet impinging on the working electrode surface in an operative condition.

As mentioned above, the distance S is 0.5–1 mm. The jet diameter is determined by the nozzle diameter is also 0.3 mm. The liquid jet forces a path through the bulk solution, generally indicated by reference numeral 48 so that the jet impinges at the center of the working electrode 36. The working electrode 32 diameter is typically 3 mm in the preferred structure. When the jet hits the working electrode it spreads out radially and disperses as it approaches the outer edges of the electrode 32. Three different hydrodynamic conditions are set up; firstly a diffusion stationary layer 50 is set up adjacent to the surface of the electrode and this is typically a few tens of microns in thickness. The hydrodynamic boundary layer indicated by reference numeral 52 is a region where flow is well defined and is typically 1–2 mm in thickness. Outside the hydrodynamic boundary layer lies the bulk solution 48 where mass transport is unable to influence the electrode response because it is far away from the electrode's surface.

FIGS. 1–3 relate to the preferred embodiment of the invention. However, it would be appreciated that there may be various modifications to this.

Figure 4A:
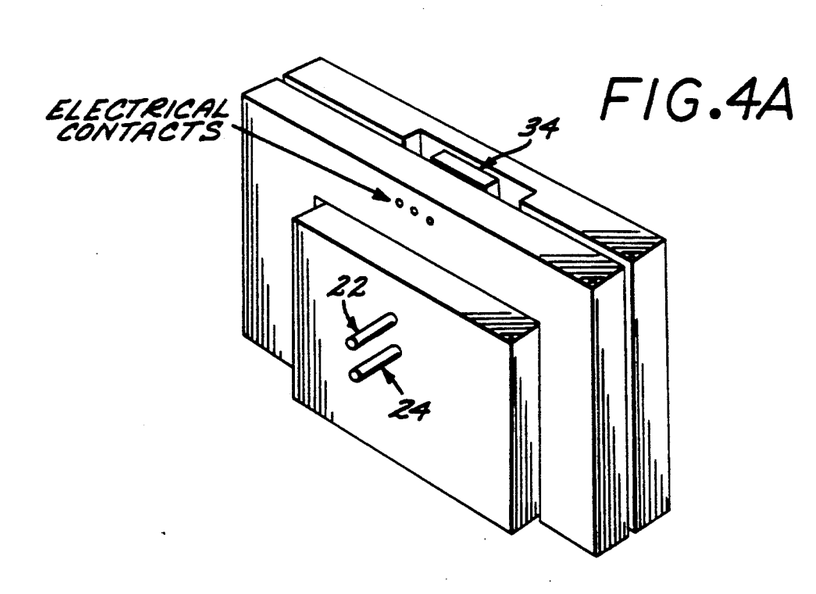
FIG. 4 is a perspective view of another design of preferred embodiment of the wall-jet voltammetric detector
Figure 4B:
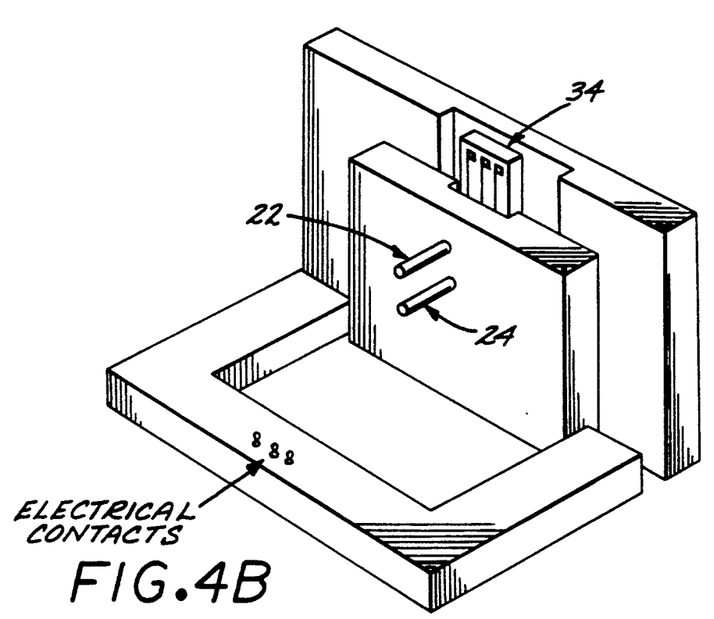

For example, reference is now made to FIG. 4 of the drawings which shows a modified design of the preferred embodiment of the wall-jet detector. In this design a simple means of providing electrical contact to conducting leads of the electrodes screen printed on the slide (34). Electrical contact is made when the detector is in the closed position as shown in FIG. 4(a). In the open position shown in FIG. 4(b), the electrode slide (34) can be easily removed and a fresh slide fitted in.

Figure 5:
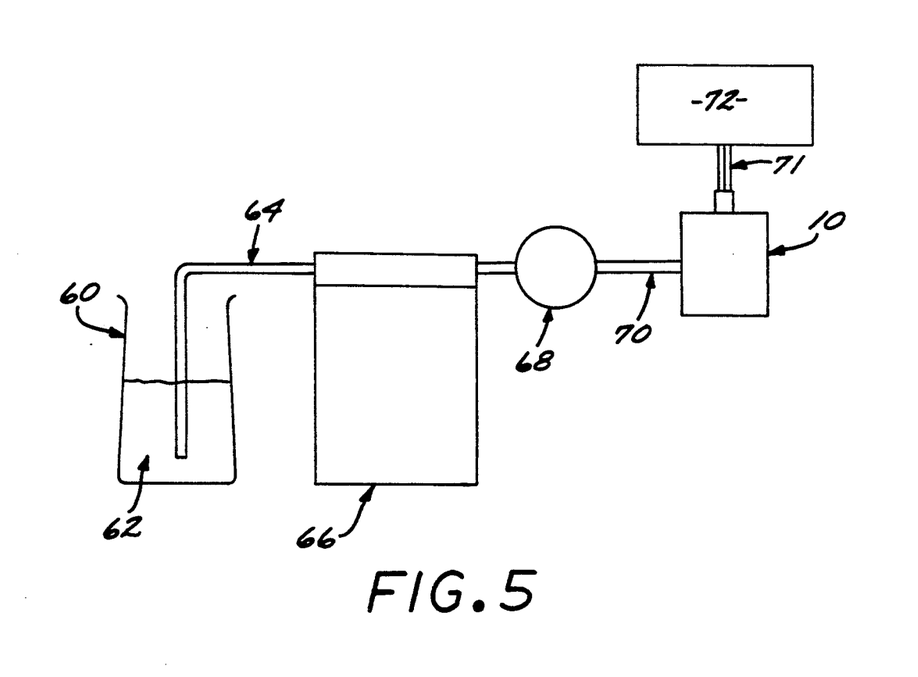
FIG. 5 is a schematic diagram of a system for detecting electrochemical species incorporating the wall jet detector shown in FIG. 1.

Reference is now made to FIG. 5 of the drawings which is a schematic representation of the system for detecting electrochemical species. A flask 60 containing a solution 62 with electroactive species is connected by a conduit 64 to a peristaltic pump 66. The conduit passes through the pump and is connected to a flask 68 which is designed to be half full of liquid to form a pulse damping system. The outlet from the pulse damping system is connected via conduit 70 to the nozzle 42 of the wall-jet detector 10 to provide a liquid jet 46 as hereinbefore described. The electrochemical species detected by the working electrode 32 are coupled via conductors 71 to a measurement device 72 for obtaining typical current-voltage curves in response to the particular electrochemical species detected. The measurement device typically could be any commercial polarographic or voltammetric analyser such as the model 174 (Princeton Applied Research).

Figure 6:
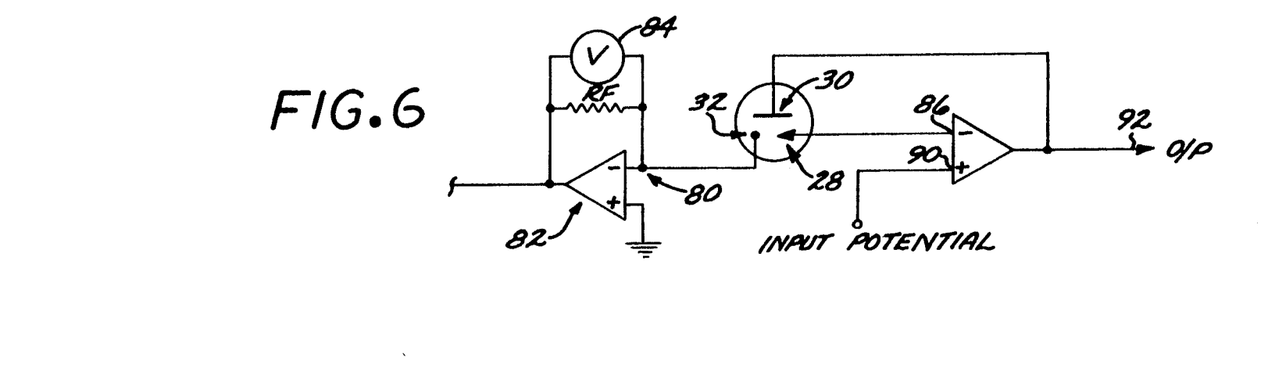
FIG. 6 is a circuit diagram showing the control circuit for detecting electrochemical species.

Reference is now made to FIG. 6 of the drawings which shows a typical electrical circuit used to apply the potential difference between the working and reference electrodes and measure the signal current flowing through the wall-jet cell FIG. 1) due to the detected electrochemical species. The working electrode 36 is connected to the inverting input 80 of an operational amplifier 82 in which the non-inverting (+) input is connected to ground and a suitable resitor Rf is incorporated in the feedback loop. The potential drop across the feedback resistor is measured by a voltmeter 84 and the amplifier acts as a current-to-voltage converter. The reference electrode 28 is connected to the inverting input 86 of amplifier 88 and an applied potential from a voltage source, connected to the non-inverting input 90. The output 92 of the amplifier is fed to the counter electrode 30 which is in the wall-jet detector 10. This acts to maintain the reference electrode at the input potential 92. While other electronic control and measurement configurations may be used this preferred potentiostatic arrangement enables accurate and sensitive measurement of the cell current.

EXAMPLE 1

Aniodic Stripping Voltammetry

Figure 7:
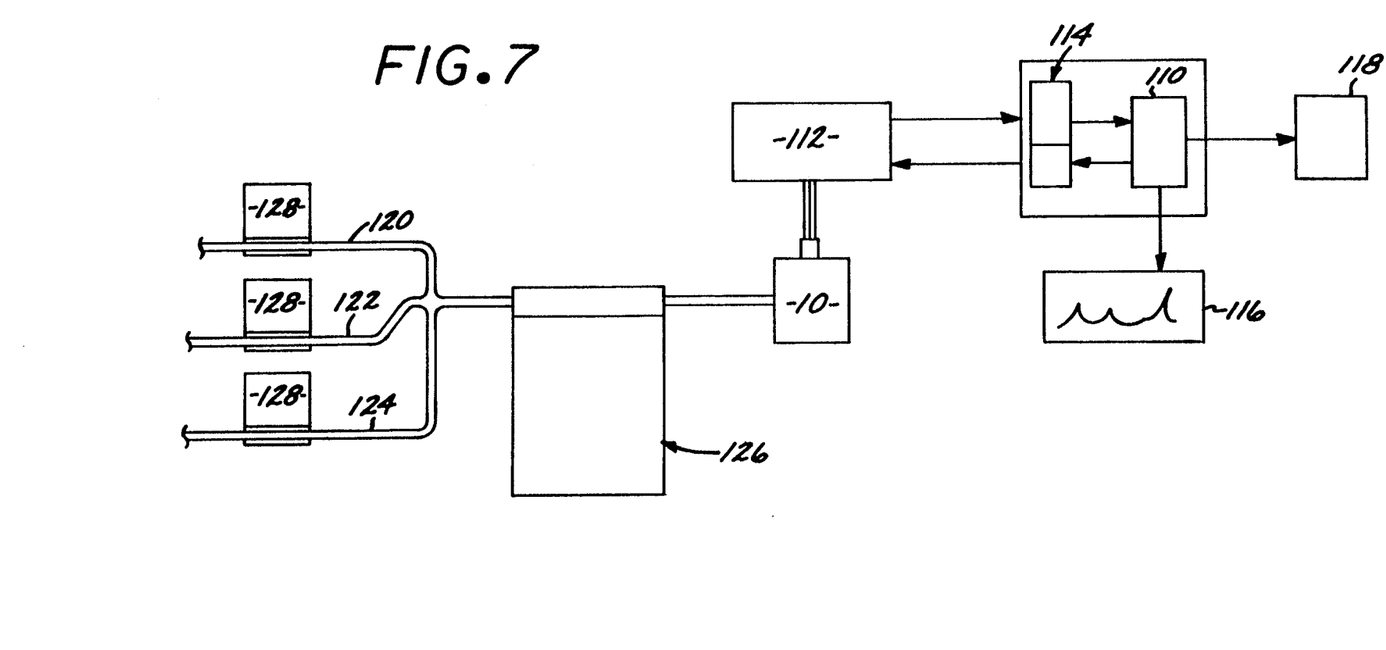
FIG. 7 is a schematic diagram of an exemplary instrumentation and solvent delivery system.

Use of the wall jet detector described with reference to FIGS. 1–4 will now be given by way of example in automated hydrodynamic anodic stripping voltammetry (HASV) with a mercury film wall jet electrode. FIG. 7 shows an exemplary control instrument solvent delivery system used in HASV. The structure is similar to that shown in FIG. 5, however, a single-chip microprocessor 110 was interfaced to a purpose-built potentiostat 112 via an electronic interface 114. The interface consists of a 12 bit digital-to-analogue converter and a 12 bit analogue-to-digital converter. The HASV scans were plotted on a liquid crystal display 116 or on a digital plotter 118 via a serial RS232 communication line for a hard copy.

Referring in more detail to FIG. 7, it will be seen that mercury, blank electrolyte and sample solutions 120, 122, 124 respectively are delivered by separate streams by persitaltic pump 126. Pinch valves 128 were used to select mercury, sample or standard solutions.

Stock sample solutions of lead and copper were prepared by dissolving the metal salt in 0.5 M nitric acid. Mercury solutions were prepared by dissolving triply distilled mercury in nitric acid and required standards were made by diluting to appropriate concentrations. The blank electrolyte solution was 0.1M KN03/0.005M nitric acid.

In the case of ASV, a stable film is formed at the wall jet electrode only when the thickness of the film is less than the diffusion layer. As indicated above, the thickness of the diffusion layer, d, is given by $$d = 2.3\, D^{\frac{1}{3}} a^{1} v^{5/12} R^{5/4} V^{-\frac{3}{4}} \qquad (1)$$

where D is the diffusion coefficient, a is the inlet diameter, v is the kinematic viscosity, R is the radius of the working electrode and V the solution volume flow rate. The flow rate range implied was 1–3 ml per minute and in this case the diffusion layer thickness was of the order of 10 um.

Although the cell design of the preferred embodiment of the invention defines a large cell volume, because of the flow properties of the wall jet, only species from the jet can reach the electrode surface. Thus, the ASV plating, hold and stripping operations can be performed in different solutions without having to flush out the cell. Moreover, by using small jet inlet diameters, less than 0.5 mm, it is feasible to use very small solution volumes at each step, in some cases as low as a few microlitres and consequently it is possible to choose the optimum solution for each operation. A further advantage of the wall jet electrode in ASV is that the mercury film can be preplated prior to plating the sample metal ions that are to be analysed.

Figure 8:
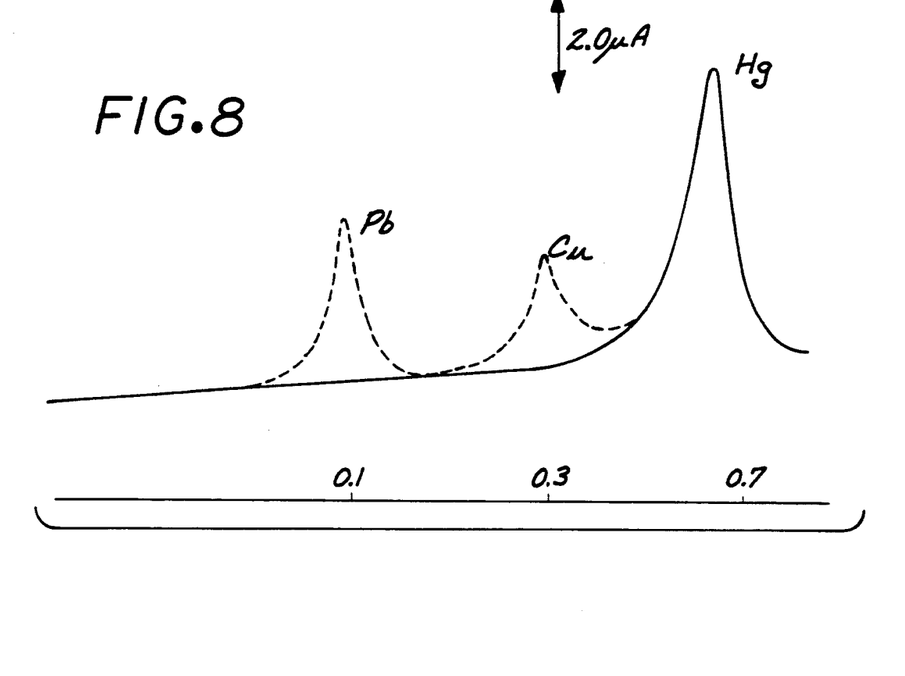
FIG. 8 shows typical hydrodynamic anodic stripping voltammetry plots in the differential pulse mode for lead, copper, cadmium and zinc, and the corresponding background plot using a conductive carbon electrode and wall-jet detector of FIG. 1 and instrumentation and solvent delivery system of FIG. 6.

FIG. 8 shows typical differential pulse HASV current-potential plots for lead and copper at a mercury-film wall-jet electrode and the corresponding background plot. In this example the working electrode consists of a carbon working electrode on which a mercury film has been preplated. The mercury film is further coated with a thin layer of Nafion, a perfluorinated cation exchange polymer made by Dupont.

Use of microprocessor control permits subtle control of ASV at the wall jet electrode and the computer also enables accurate control of solution stream selection, control of the pre-electrolysis potentials, timing and synthesis of the applied potential waveform and control of data acquisition. It will also be appreciated that the computer can further process experimental data, for example, by background subtraction and digital filtering.

EXAMPLE 2

Flow Injection Analysis

When a discrete sample is injected into the electrode as in HPLC or flow injection analyses (FIA) dispersion of the sample takes place in the hydrodynamic boundary layer and not in the bulk solution as is usually imagined. The dispersion penetrates into the diffusion layer where the region of electrochemical reaction occurs; this is where electrochemical species are sensed by working electrode 32. It is very important that the liquid jet operates under laminar flow conditions which is, in turn, governed by the stability of the jet impinging on the electrode. The stability of a free jet is given by the dimensionless Reynolds number, $Re = Ul/v$ where $U$ is the linear flow velocity, $l$ is the jet inlet diameter and $v$ is the kinematic viscosity. It will be appreciated that each of the parameters in the Reynolds number can be varied in the relation to each other such that the dimensionless Reynolds number will still define the laminar flow conditions. This gives flexibility in the design of the structure and the operating conditons to suit detection of particular electroactive species.

The sensitivity of the detector depends of course on the concentration of electroactive material in the known diffusion layer. The limiting current $$i_{lim} = nFADC/dl \quad (2)$$

where n is the number of electrons transferred in the electrode process, F is Faraday's constant, A is the electrode area, D is the diffusion coefficient, and C is the concentration of the electroactive species and dl is the diffusion layer thickness. The limiting current, i , is a steady state response which is inversely proportional to the diffusion layer's thickness. therefore it will be appreciated from equation (2) that increasing the thickness of the diffusion layer reduces the limiting current and of course the sensitivity of the detector. Therefore in the arrangement by selection of the outward parameters of L,S and d the diffusion layer is minimised to result in maximum sensitivity of the detector. In addition, by minimising the hydrodynamic boundary layer thickness, dispersion of the analyte towards the boundary layer is greatly decreased and band spreading is minimised.

Figure 9:
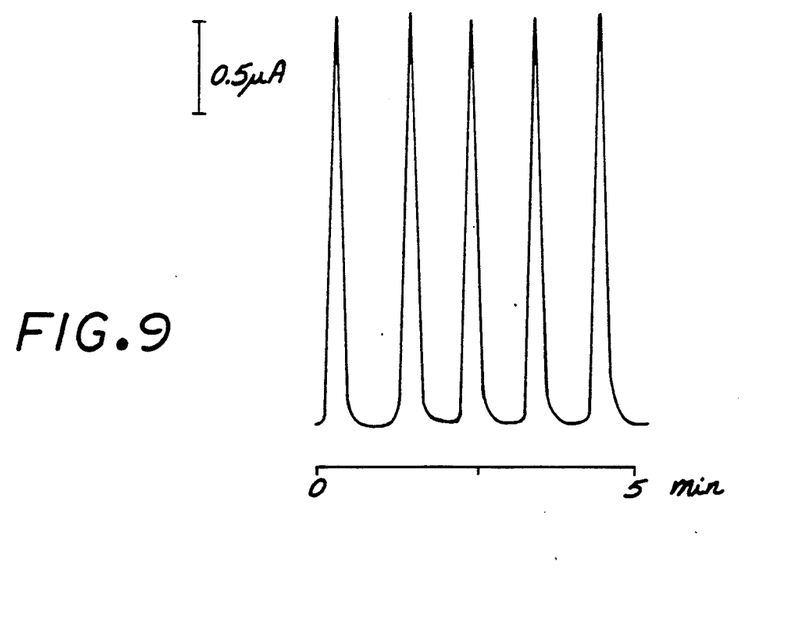
FIG. 9 shows typical flow-injection peaks for successive injections of ferrocyanide using a conductive carbon working electrode and wall-jet detector of FIG. 1.

Reference is now made to FIG. 9 of the drawings which shows typical profiles for successive injections of a sample of 5 mM ferrocyanide. These results were obtained using the experimental setup described in FIG. 5 where the sample volume is 20 μl.

One of the benefits of the wall-jet detector in FIA is that rapid sample throughput (100 samples per hour), small sample volume (10 μl) and high precision (less than 1%) are feasible.

EXAMPLE 3

High-Pressure Liquid Chomatography (HPLC)

Figure 10:
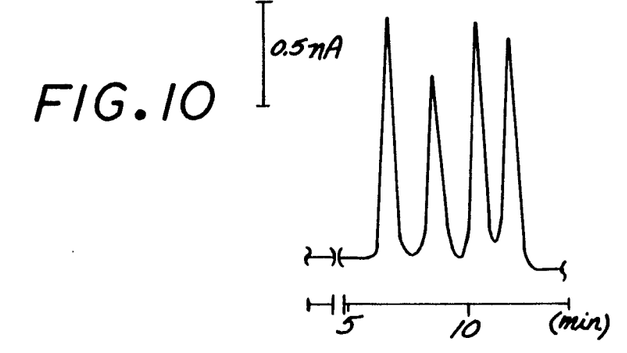
FIG. 10 shows typical HPLC peaks for the separation of a number of catecholamines at the conductive carbon carbon electrode and wall-jet detector.

Reference is now made to FIG. 10 which shows typical amperometric chromatograms for the separation of several catecholamines of clinical interest separated on an ion-exchange HPLC system using a buffered eluent of pH 5.5. In this application the carbon working electrode 32 is held at a positive potential of +0.5 V vs the Ag/AgCl reference electrode 28. At this potential the catecholamines are oxidised. The preferred distance S between the inlet nozzle and the working electrode 32 is 2 mm.

The advantage of the disposable wall-jet electrode system lies in the ability to change electrodes after each analysis. In the case of the catecholamines given in this example gradual poisoning of the electrode surface occurs with continuous use because of adsorption of products of the catecholamine electro-oxidation and the adsorption of impurities. Impurities are of particular concern in the analysis of biological fluids.

EXAMPLE 4

Blood Glucose Analysis

Figure 11:
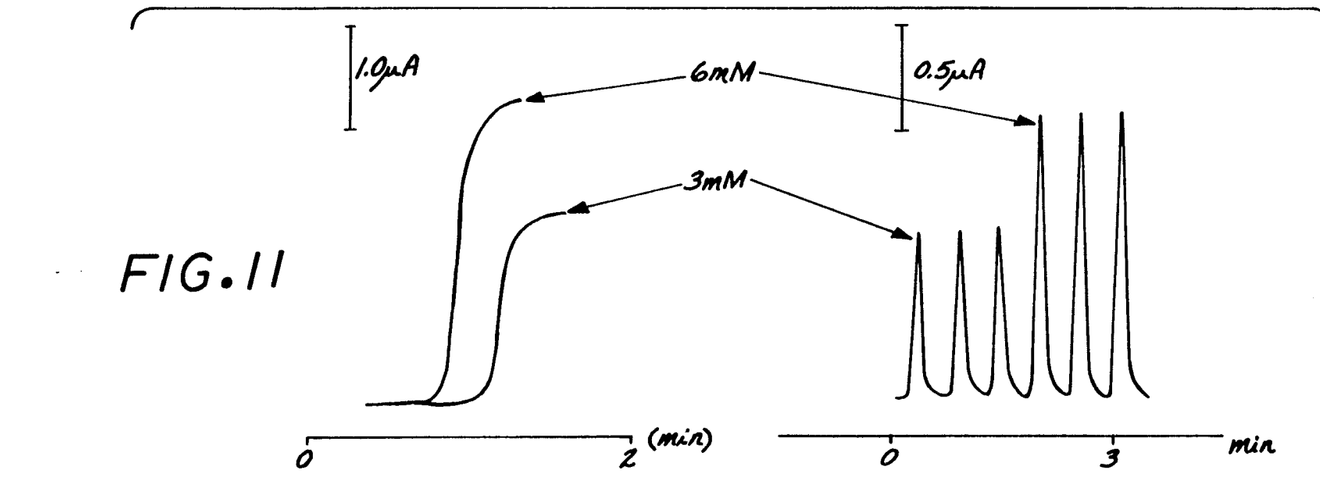
FIG. 11 compares steady state and flow-injection peak profiles for the analysis of blood-glucose.

Reference is now made to FIG. 11 which shows typical flow-injection (a), and steady-state (b), current-time responses for the analysis of 10.0 mM glucose in human whole blood using the flow-system described in FIG. 4.

In this example the working electrode 32 is an enzyme electrode where the base carbon electrode is coated with a glucose oxidase-mediator reagent layer. This layer is then covered with a cellulose acetate membrane by dip coating. The membrane is permeable to glucose but excludes larger species such as blood cells and protein molecules. The carbon working electrode is held at an operating potential of +0.2 V vs Ag/AgCl reference electrode 28.

In the flow-injection mode the blood sample volume is 10 ul. Thus the detector gives a transient peak-shaped response. In the steady-state mode, however, the sample volume is about 250 ul. The carrier flow rate is 0.5 ml/min.

It will be appreciated that various modifications may be made to the embodiment herein

What is claimed is:

1. A wall-jet detector for detecting electrochemical species in continuous-flow monitoring, comprising:

a detector cell having an internal chamber of large solution volume where the chamber is open at one end;

a liquid jet producing means coupled tothe cell housing for providing a liquid jet having a jet direction into said chamber and said liquid jet producing means defining a liquid jet inlet to said chamber;

a working electrode fabricated on a flat, rectangular slide that is slidably positioned in said cell chamber opposite to said liquid jet inlet at a predetermined distance therefrom, and said working electrode lying in a plane substantially perpendicular to the direction of said liquid jet inlet;

a reference electrode coupled to the cell and extending into said chamber and positioned outside the boundary layer of said liquid jet;

a counter electrode coupled tothe cell; and a liquid outlet means for permitting the outflow of solution from said chamber where the outlet controls the solution level in the cell chamber so that the level is above the working 2. The wall jet detector of claim 1 wherein the arrangement being such that in operative condition, a jet of liquid of a predetermined cross-sectional area is forced into said chamber through said liquid jet inlet means, said working electrode having an electrode cross-sectional area of at least five times the cross-sectional area of the liquid jet, said working electrode and said reference electrode being energised for said working electrode to detect electrochemical species in said jet impinging on said working electrode, 3. A wall-jet detector as claimed in claim 1 wherein each of said counter electrode and reference electrode are movable and each has respective locking means associated therewith for permitting respective said counter electrode and said reference electrode to be moved and positioned relative to the said working electrode.

4. A wall jet detector as claimed in claim 1 wherein said counter electrode is symmetrically positioned in said chamber with respect to said liquid jet inlet and working electrode.

5. A well-jet detector as claimed in claim 1 wherein said working electrode has a circular flat surface with the center of the flat surface being located along the axis of the liquid jet inlet.

6. A wall jet detector as claimed in claim 1 wherein said working electrode cross-sectional area is 5 to 10 times the cross-sectional area of the liquid jet cross-sectional area.

7. A wall jet detector as claimed in claim 1 wherein the working electrode is a disk made of carbon, platinum or gold fabricated on a disposable flat rectangular slide.

8. A wall-jet detector as claimed in claim 1 wherein at least two spaced working electrodes are provided on a single slide, each working electrode, in use, detecting electroactive species at different potentials.

9. A wall jet detector as claimed in claim 1 wherein the working electrode is a micro-electrode array where the width of the electrode is between 1 and 50 microns.

10. A wall-jet detector as claimed in claim 1, wherein the slide is made of a material selected from the group consisting of glass, ceramic, and plastic.

11. A wall-jet detector as claimed in claim 1, wherein the working electrode is made by screen printing conductive carbon ink.

12. A wall-jet detector as claimed in claim 1, wherein the working electrode is made by screen printing organic metal ink on the slide and thereafter the slide is fired.

13. A wall-jet detector as claimed in claim 1, wherein the working electrode is made by photolithographic and vapor deposition techniques.

14. A wall-jet detector as claimed in claim 1, wherein the working electrode is modified with a chemical coating to make the electrode sensitive to a specific chemical species.

15. A wall-jet detector as claimed in claim 14, wherein the chemical coating is selected from the group consisting of a mercury film and a mercury film covered with a polymer layer.

16. A wall-jet detector as claimed in claim 14, wherein the chemical coating is an enzyme.

17. A wall-jet detector as claimed in claim 14, wherein the chemical coating is a mixture of several chemicals.

18. A wall-jet detector as claimed in claim 14, wherein the chemical coating is a membrane to provide a diffusion barrier to chemical species.

19. A wall jet detector as claimed in claim 1 wherein the reference electrode is a silver-silver chloride and the counter electrode is made of carbon or platinum.

20. A well jet detector as claimed in claim 1 wherein the reference electrode is not sealed and employs a flowing internal filling solution, thereby providing a flowing liquid junction.

* * * * *